(12) United States Patent
Vilsmeier

(10) Patent No.: US 10,395,420 B2
(45) Date of Patent: Aug. 27, 2019

(54) CALCULATION OF A MEDICAL IMAGE USING TEMPLATES

(75) Inventor: Stefan Vilsmeier, Munich (DE)

(73) Assignee: Brainlab AG, Munich (DE)

(*) Notice: Subject to any disclaimer, the term of this patent is extended or adjusted under 35 U.S.C. 154(b) by 442 days.

(21) Appl. No.: 13/406,810

(22) Filed: Feb. 28, 2012

(65) Prior Publication Data
US 2013/0222415 A1    Aug. 29, 2013

(51) Int. Cl.
*G06T 15/50* (2011.01)
*G06F 19/00* (2018.01)
*A61B 8/00* (2006.01)

(52) U.S. Cl.
CPC ............ *G06T 15/503* (2013.01); *A61B 8/461* (2013.01); *G06F 19/321* (2013.01); *G06T 2210/41* (2013.01); *G09G 2340/045* (2013.01); *G09G 2340/12* (2013.01); *G09G 2380/08* (2013.01)

(58) Field of Classification Search
CPC ...... G06F 19/321; G06F 17/30; G06F 19/366; G06F 17/30265; G06F 19/322; G06F 19/3418; G06F 19/3481; G06F 11/30; G06F 11/3048; G06F 19/3487; G06F 19/345; G06F 17/30864; G01V 1/28; G01V 1/42; G01V 1/30; H04N 5/2259; H04N 5/23238; H04N 5/2628; G06T 15/503
See application file for complete search history.

(56) References Cited

U.S. PATENT DOCUMENTS

| | | | |
|---|---|---|---|
| 2005/0254707 A1* | 11/2005 | Takahashi | G06T 5/009 382/169 |
| 2006/0112334 A1* | 5/2006 | Endrikhovski | G06F 3/013 715/700 |
| 2008/0118139 A1* | 5/2008 | Huo | G06T 5/009 382/132 |
| 2009/0059082 A1* | 3/2009 | Jakobovits | G06F 16/51 348/673 |
| 2010/0049740 A1* | 2/2010 | Iwase | G06Q 10/06 705/7.27 |
| 2010/0114597 A1* | 5/2010 | Shreiber | G06F 19/321 705/2 |
| 2010/0128946 A1* | 5/2010 | Fidrich et al. | 382/131 |
| 2011/0206260 A1* | 8/2011 | Bergmans | G01R 33/543 382/131 |
| 2012/0035963 A1* | 2/2012 | Qian | G06F 19/3487 705/3 |
| 2012/0051609 A1* | 3/2012 | Avinash | G06T 7/0014 382/128 |
| 2012/0131507 A1* | 5/2012 | Sparandara | G06F 19/322 715/833 |
| 2013/0083979 A1* | 4/2013 | Vilsmeier | 382/128 |
| 2013/0135287 A1* | 5/2013 | McCabe et al. | 345/419 |
| 2014/0155730 A1* | 6/2014 | Bansal | G01V 3/14 600/409 |

* cited by examiner

*Primary Examiner* — James A Thompson
(74) *Attorney, Agent, or Firm* — Tucker Ellis LLP

(57) ABSTRACT

A data processing method for calculating a medical display image to be displayed on a display device, comprising the steps of acquiring at least one image dataset representing a medical image of a patient, acquiring a patient-specific information dataset representing patient-specific information and calculating the display image from the at least one image dataset on the basis of a template, the template being selected from a plurality of templates in accordance with the acquired patient-specific information.

20 Claims, 2 Drawing Sheets

CALCULATION OF A MEDICAL IMAGE USING TEMPLATES

Figure 1:
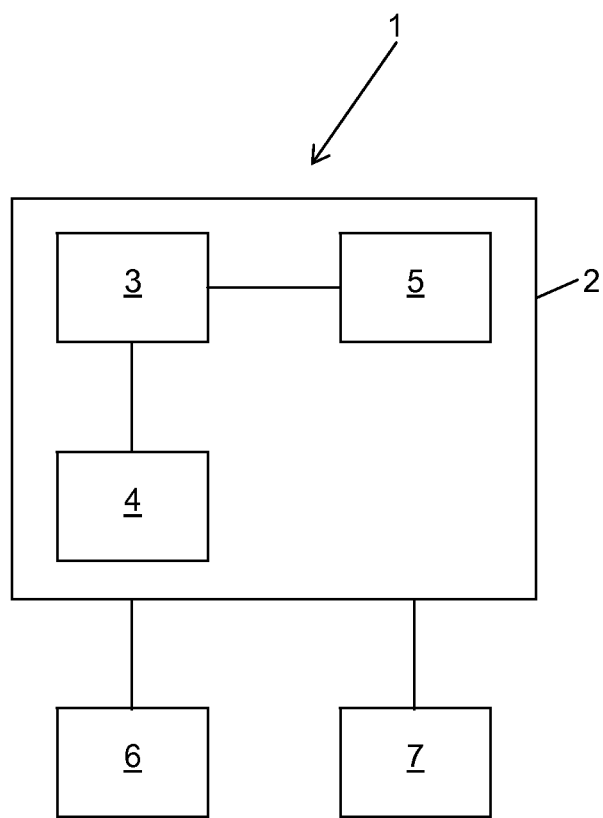

The present invention relates to a data processing method, a program and a device for calculating a medical display image to be displayed on a display device using a template.

It is well-known to create a medical image dataset representing a medical image of a patient using a suitable imaging modality. Depending on the modality, the image dataset typically is either a 2D or 3D dataset, representing a two-dimensional or three-dimensional image. However, such an image dataset can typically not be directly displayed on a display device. It is therefore necessary to calculate a display image from the image dataset. It shall be noted that the display image is preferably a two-dimensional image, but can also be a three-dimensional image or a sequence of images, for example a sequence of images showing an object from varying viewing angles.

The present invention relates to a data processing method for calculating a medical display image to be displayed on a display device. The method comprises a step of acquiring at least one image dataset representing a medical image of a patient. The method further comprises the step of acquiring a patient-specific information dataset representing patient-specific information. The method still further comprises the step of calculating the display image from the at least one image dataset on the basis of a template, wherein the template is selected from a plurality of templates in accordance with the acquired patient-specific information.

The image dataset can be generated using any suitable imaging method. In the field of medicine, imaging methods are used to generate image data (for example, two-dimensional or three-dimensional image data) of anatomical structures (such as soft tissues, bones, organs, etc.) of the human body. Medical imaging methods are understood to mean advantageously apparatus-based imaging methods (so-called medical imaging modalities and/or radiological imaging methods), such as for instance computed tomography (CT) and cone beam computed tomography (CBCT; in particular volumetric CBCT), x-ray tomography, magnetic resonance tomography (MRT or MRI), conventional x-ray, sonography and/or ultrasound examinations, and positron emission tomography (PET). Analytical devices are in particular used to generate the image data in apparatus-based imaging methods. The imaging methods are in particular used for medical diagnostics, to analyse the anatomical body in order to generate images which are described by the image data. The imaging methods are in particular used to detect pathological changes in the human body. A tumor for example represents an example of a change in an anatomical structure.

Within this document, another suitable imaging method would be photography which generates a two-dimensional photographic medical image, for example in the visible, infrared or ultraviolet spectrum or a combination thereof.

The expression "acquiring data" encompasses in particular (within the framework of a data processing method) the scenario in which the data are determined by the data processing method or program. Determining data in particular encompasses measuring physical quantities and transforming the measured values into in particular digital data and/or computing the data by means of a computer, in particular computing the data within the method of the invention. The meaning of "acquiring data" in particular also encompasses the scenario in which the data are received or retrieved by the data processing method or program, for example from another program, a previous method step or a data storage medium, in particular for further processing by the data processing method or program. Thus, "acquiring data" can also for example mean waiting to receive data and/or receiving the data. The received data can for example be inputted via an interface. "Acquiring data" can also mean that the data processing method or program performs steps in order to (actively) receive or retrieve the data from a data source, for instance a data storage medium (such as for example a ROM, RAM, database, hard disc, etc.) or via the interface (for instance, from another computer or a network). The data can achieve the state of being "ready for use" by performing an additional step before the acquiring step. In accordance with this additional step, the data are generated in order to be acquired. The data are in particular detected or captured (for example, by an analytical device). Alternatively or additionally, the data are inputted in accordance with the additional step, for instance via interfaces. The data generated can in particular be inputted (for instance, into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. Thus, "acquiring data" can also involve commanding a device to obtain and/or provide the data to be acquired. The acquiring step in particular does not involve an invasive step which would represent a substantial physical interference with the body requiring professional medical expertise to be carried out and entailing a substantial health risk even when carried out with the required professional care and expertise. Acquiring, in particular determining, data in particular does not involve a surgical step and in particular does not involve a step of treating a human or animal body using surgery or therapy. This also applies in particular to any steps directed to determining data. In order to distinguish the different data used by the present method, the data are denoted (i.e. referred to) as "XY data" and the like and are defined by the information which they describe which is preferably called "XY information".

The patient-specific information generally describes the condition and/or circumstances of a particular patient.

In many cases, the image dataset comprises more information than the information to be displayed on the display device. It is therefore required to provide settings according to which the display image is to be calculated from the image dataset. Typically, the image dataset is a three-dimensional dataset, while the display is a two-dimensional image. By using a template, at least some and preferably all settings required for calculating the display image from the image dataset are pre-defined in the template and do not have to be set manually. A template therefore is a dataset which comprises the settings or rules for calculating the display image from an image dataset. An appropriate template is selected depending on the acquired patient-specific information.

In one preferred embodiment, the patient-specific information comprises a type or a category of a disease of the patient. The type or category is preferably defined in accordance with a classification. One such suitable classification is the ICD (International Classification of Diseases) as provided by the WHO. The disease is in particular a tumor. A suitable classification in this case can for example use ICD tumor codes.

If the disease is a tumor, then the step of calculating the display image optionally comprises highlighting the contour of the tumor in the display image. Known techniques can be applied for identifying the tumor either in the image dataset or the display image. The known techniques comprise segmentation. One option for highlighting the contour is to colorize the contour or the whole tumor in the display image.

In another embodiment, the patient-specific information comprises information on at least one of a medical indication, a prior treatment, a prior disease, a planed treatment, a following treatment step and an applied contrast agent. Any one or more of these information can be used to select an appropriate template.

The medical indication represents appropriate medical actions to be taken for a certain disease pattern. A prior treatment represents one or more medical actions which have already been performed on the patient. Different steps of a medical workflow can require different settings for the calculation of the display image, such that the next treatment step in the workflow can influence the selection of the template. The applied contrast agent means the contrast agent which was applied for generating the image dataset. It shall be noted that neither the prior treatment nor applying the contrast agent are a part of the present invention. The present invention only uses information on these steps.

In one embodiment, the image dataset represents a three-dimensional medical image and the step of calculating the display image comprises selecting a sectional plane in accordance with the template. The sectional plane means the orientation and the position of the plane of the display image within the image dataset.

In another embodiment, a plurality of image datasets have been acquired and the step of calculating the display image comprises selecting at least one of the image datasets in accordance with the template for calculating the display image. In other words, the template defines which one or more of the image datasets are used as input datasets for calculating the display image. The image datasets can for example represent medical images captured using different imaging methods, captured from different viewing angles, captured at different points in time or any combination thereof. As an option, two or more image datasets are registered with each other. Image registration is the process of transforming different image datasets into one common coordinate system. Registration is preferably used in order to be able to compare or integrate the data of different image datasets. Two or more image datasets can preferably be registered using elastic fusion.

Elastic fusion transformations (e.g. image fusion transformation) are in particular designed to enable a seamless transition from one data set (e.g. first data set, e.g. first image) to another data set (e.g. second data set, e.g. second image). The transformation is in particular designed such that one of the first and second data sets (images) is deformed, in particular in such a way that corresponding structures (in particular, corresponding image elements) are arranged at the same position as in the other of the first and second images. The deformed (transformed) image which is transformed from one of the first and second images is in particular as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are in particular vectors of a deformation field F. These vectors are determined by the optimisation algorithm which results in an optimum degree of similarity. Thus, the optimum degree of similarity represents a condition, in particular a constraint, for the optimisation algorithm. The bases of the vectors lie in particular at voxel positions of one of the first and second images which is to be transformed, and the tips of the vectors lie at the corresponding voxel positions in the transformed image. A plurality of these vectors are preferably provided, for instance more than twenty or a hundred or a thousand or ten thousand, etc. Preferably, there are (other) constraints on the transformation (deformation), in particular in order to avoid pathological deformations (for instance, all the voxels being shifted to the same position by the transformation). The constraints include in particular the constraint that the transformation is regular, which in particular means that a Jacobian determinant calculated from a matrix of the deformation field (in particular, the vector field) is larger than zero. The constraints include in particular the constraint that the transformed (deformed) image is not self-intersecting and in particular that the transformed (deformed) image does not comprise faults and/or ruptures. The constraints include in particular the constraint that if a regular grid is transformed simultaneously with the image and in a corresponding manner, the grid is not allowed to interfold at any of its locations. The optimising problem is in particular solved iteratively, in particular by means of an optimisation algorithm which is in particular a first-order optimisation algorithm, in particular a gradient descent algorithm. Other examples of optimisation algorithms include optimisation algorithms which do not use derivations such as the downhill simplex algorithm or algorithms which use higher-order derivatives such as Newton-like algorithms. The optimisation algorithm preferably performs a local optimisation. If there are a plurality of local optima, global algorithms such as simulated annealing or genetic algorithms can be used. In the case of linear optimisation problems, the simplex method can for instance be used.

In the steps of the optimisation algorithms, the voxels are in particular shifted by a magnitude in a direction such that the degree of similarity is increased. This magnitude is preferably less than a predefined limit, for instance less than $1/10$ or $1/100$ or $1/1000$ of the diameter of the image, and in particular about equal to or less than the distance between neighbouring voxels. Due in particular to a high number of (iteration) steps, large deformations can be implemented.

The template can comprise rules for combining information from different image datasets into one display image, for example by blending views generated from different image datasets or placing different views in the display image.

In another embodiment, the step of calculating the display image comprises selecting at least one of windowing parameters, a zoom factor and a cut-out in accordance with the template. Windowing describes the process of adapting the dynamic range of the image dataset to the dynamic range of the display device. Typical display devices have a limited color depth, for example of 24 bit, which means 8 bit or 256 steps per color. However, imaging methods can create image datasets of a higher dynamic range such as 16 bit, 24 bit, 32 bit or even more. So mapping the whole dynamic range of the image dataset to the color depth of the display image, in particular to a single color range such as a grey scale, leads to a loss of information. So instead of compressing the dynamic range of the image dataset to the color depth of the display image, a window of the dynamic range of the image dataset is used for calculating the display image, while the rest of the dynamic range is discarded. It is further possible to define a plurality of windows for the dynamic range and to map the different windows individually to the color depth of the display image.

By using windowing, a range of interest of the dynamic range of the image dataset can be analyzed. The range of interest depends on the object to be analyzed, such as a bone, an organ or a tumor. This is particularly useful if the dynamic range of the image dataset is calibrated. The image dataset is either directly calibrated by the apparatus used for imaging or by adapting the dynamic range to a suitable reference.

The zoom factor describes the magnification which is used when calculating the display image from an image dataset. This is particularly useful if the resolution of the image dataset is higher than the resolution of the display image. A cut-out in particular describes an area within the image dataset which is to be used when calculating the display image, while information outside this area is disregarded. This is particularly useful to block out structures next to an object of interest in the display image.

One aspect of the present invention is to select a suitable template from the plurality of templates. This selection is based on the acquired patient-specific information. In one embodiment, the invention comprises the step of acquiring a lookup table comprising a plurality of lookup table patient-specific information datasets and of assigning one of the plurality of the templates to each of the lookup table patient-specific information datasets, wherein the template used for calculating the display image is selected using the lookup table. Each lookup table patient-specific information dataset thus has an associated template, wherein the same template can be associated with just one lookup table patient-specific information dataset, a plurality of lookup table patient-specific information datasets or all lookup table patient-specific information datasets in the lookup table. In particular, the lookup table is searched for a lookup table patient-specific information dataset corresponding to the acquired patient-specific information dataset. This search process is particularly effective if the patient-specific information comprises a type or a category of a disease as described above.

Searching the lookup table is straight-forward if the acquired patient-specific information dataset exactly matches one of the lookup table patient-specific information datasets. In order to handle all cases, an embodiment is proposed in which the step of selecting the template comprises calculating distance measures between the acquired patient-specific information dataset and each of the lookup table patient-specific information datasets, determining the lookup table patient-specific information dataset with the lowest distance measure and selecting the template associated with this lookup table patient-specific information dataset. The approach for calculating a distance measure preferably depends on the (kind of) information contained in the acquired patient-specific information dataset. Suitable weighting factors can be assigned to different information in the acquired patient-specific information dataset. The calculation of a distance measure can be based on a mathematical formula, a lookup table comprising distance values for certain information or a combination thereof. Such a lookup table can for example comprise distance values for combinations of categories in a classification system.

In another embodiment, the step of calculating the display unit comprises adding diagnosis-specific information to the display image in accordance with the template. This means that the display image does not only comprise information taken from the image dataset, but further information which is specific to the diagnosis for the patient. The diagnosis-specific information in particular comprises information on at least one of a landmark, a functional area, the patient's anatomy, a therapy, the path of a treatment beam, a trajectory and an access plan.

In a case of a landmark or a functional area, a corresponding part of the display image is preferably highlighted, in particular using a certain color. A landmark is a defined element of an anatomical body part which is always identical or recurs with a high degree of similarity in the same anatomical body part of multiple patients. Typical landmarks are for example the epicondyles of a femoral bone or the tips of the transverse processes and/or dorsal process of a vertebra. A landmark which lies on (in particular on the surface of) a characteristic anatomical structure of the body part can also represent said structure. The landmark can represent the anatomical structure as a whole or only a point or part of it. A landmark can also for example lie on the anatomical structure, which is in particular a prominent structure. An example of such an anatomical structure is the posterior aspect of the iliac crest. Other landmarks include a landmark defined by the rim of the acetabulum, for instance by the centre of the rim. In another example, a landmark represents the bottom or deepest point of an acetabulum, which is derived from a multitude of detection points. Thus, one landmark can in particular represent a multitude of detection points. A landmark can represent an anatomical characteristic which is defined on the basis of a characteristic structure of the body part. Additionally, a landmark can also represent an anatomical characteristic defined by a relative movement of two body parts, such as the rotational centre of the femur when moved relative to the acetabulum. A detection point is in particular a point on the surface of the anatomical structure which is detected, for example by a pointer.

A functional area in particular is an area of the brain which exhibits a certain function, such as the visual area, the auditory area, a motor area and so on. A treatment beam treats body parts which are to be treated. These body parts are in particular parts of a patient's body, i.e. anatomical body parts. Ionising radiation is in particular used for the purpose of treatment. In particular, the treatment beam comprises or consists of ionising radiation. The ionising radiation comprises or consists of particles (for example, sub-atomic particles or ions) or electromagnetic waves which are energetic enough to detach electrons from atoms or molecules and so ionise them. Examples of such ionising radiation are X-rays, high-energy particles (high-energy particle beams) and/or ionizing radiation emitted from a radioactive element. The treatment radiation, in particular the treatment beam, is in particular used in radiation therapy or radiotherapy, in particular in the field of oncology. For treating cancer in particular, parts of the body comprising a pathologic structure or tissue such as a tumor are treated using ionising radiation. The tumor is then an example of a treatment body part.

A trajectory can for example describe the path of an object, such as a biopsy needle, a catheter or any other medical instrument within the body of the patient. This allows for visualizing the trajectory in the display image. The access plan describes the steps which are necessary in order to reach a certain area within the body of the patient. One example for including information on an access plan in the display image is to highlight any objects or parts of objects which have to removed or relocated in order to access an object or area of interest.

Preferably, the diagnosis-specific information can be determined based on the patient-specific information dataset, in particular by using an expert system. For example, a trajectory or an access plan can be ascertained on the basis of a type or category of tumor to be treated.

It is an advantage of the present invention that a template is used to automatically calculate a display image from at least one image dataset. This means that no interaction of a user is required in order to provide the settings for calculating the display image. A further advantage is that display images for different patients and/or at different points in time are comparable if the patient-specific information datasets are identical or sufficiently similar. So if, for example, two patients have the same type of tumor, then the same template is used such that the display image is based on the same sectional plane and the same grey scale, which makes different display images easily comparable.

Another advantage is that the template can be considered as a kind of filter which reduces the amount of data. A three-dimensional image dataset may comprise several megabytes or even gigabytes of data, while a display image may only require a few hundred kilobytes.

In one embodiment, the method further comprises a step of providing the display image to a portable electronic display device. The portable electronic display device is then used to display the display image. In this case, it is not necessary that the portable electronic display device comprises the capability of storing one or more image datasets and the computational power to calculate a display image from an image dataset. Further, portable electronic display devices, such as tablet computers or mobile phones, usually have a smaller display screen than a desktop workstation. With the present invention using a template for calculating the display image, it is not necessary to display icons, scroll bars, input boxes or other control means on the screen, such that the whole screen can be used for the display image itself. It is thus easier to analyze the display image.

In one embodiment of the invention, the portable electronic display device comprises a calendar. In this embodiment, the method further comprises the steps of linking the display image stored on the portable electronic device to a calendar entry in the portable electronic display device and displaying the display image on the portable electronic display device when the calendar entry is opened. With this approach, the user of the portable electronic display device can automatically be provided with the latest information about a patient. If a new image dataset is captured, then the display image is automatically calculated using the template and transferred to the portable electronic display device. If the calendar entry indicates an appointment with a patient, then the display image corresponding to this patient is automatically linked to the calendar entry such that, upon opening the calendar entry, the display image is displayed. The user of the portable electronic display device can then easily prepare himself or herself for the appointment indicated by the calendar entry based on the latest available information.

A template may be acquired from an external source such as a database of a vendor. However, a user may manually create own templates, for example using a template editor, and associate this template to one or more patient-specific information datasets. It is further possible to create a new or modify an existing template by monitoring the settings used by a user in order to calculate a display image from an image dataset.

The method in accordance with the invention is in particular a data processing method. The data processing method is preferably performed using technical means, in particular a computer. In particular, the data processing method is executed by or on the computer. The computer in particular comprises a processor and a memory in order to process the data, in particular electronically and/or optically. The calculating steps described are in particular performed by a computer. Determining or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. The term of computer encompasses a cloud computer, in particular a cloud server. The term of cloud computer encompasses cloud computer system in particular comprises a system of at least one cloud computer, in particular plural operatively interconnected cloud computers such as a server farm. Preferably, the cloud computer is connected to a wide area network such as the world wide web (WWW). Such a cloud computer is located in a so-called cloud of computers which are all connected to the world wide web. Such an infrastructure is used for cloud computing which describes computation, software, data access and storage services that do not require end-user knowledge of physical location and configuration of the computer that delivers a specific service. In particular, the term "cloud" is used as a metaphor for the internet (world wide web). In particular, the cloud provides computing infrastructure as a service (IaaS). The cloud computer may function as a virtual host for an operating system and/or data processing application which is used for executing the inventive method. Preferably, the cloud computer is an elastic compute cloud (EC2) provided by Amazon Web Services™. A computer in particular comprises interfaces in order to receive or output data and/or perform an analogue-to-digital conversion. The data are in particular data which represent physical properties and/or are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals represent in particular the data received or outputted by the computer.

The invention also relates to a program which, when running on a computer or when loaded onto a computer, causes the computer to perform one or more or all of the method steps described herein and/or to a program storage medium on which the program is stored (in particular in a non-transitory form) and/or to a computer on which the program is running or into the memory of which the program is loaded and/or to a signal wave, in particular a digital signal wave, carrying information which represents the program, in particular the aforementioned program, which in particular comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit—CPU) which executes the computer program elements and optionally a volatile memory (in particular, a random access memory—RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. Preferably, the data storage medium is a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated into an instrument).

It lies within the scope of the present invention to combine one or more features of one or more embodiments as long as technically sensible and feasible.

The present invention shall be explained in more detail with reference to the accompanying figures. These figures show:

FIG. 1 a device for calculating a medical display image and

Figure 2:
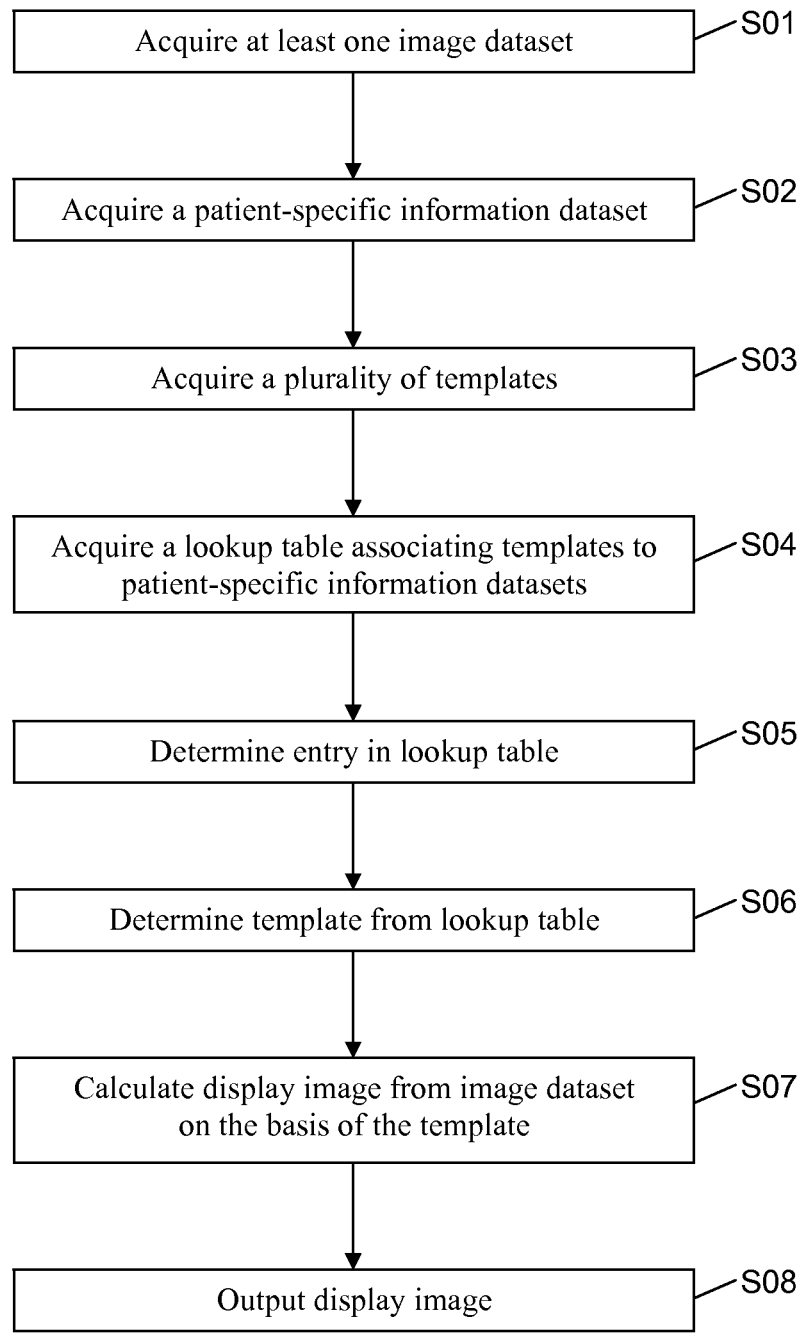

FIG. 2 a flow diagram of a method for calculating a medical display image.

FIG. 1 shows a device 1 for calculating a medical display image comprising a computer 2. The computer 2 comprises a central processing unit (CPU) 3 connected to an interface 4 and a memory 5. The computer is connected to an input device 6, such as a keyboard, a mouse, a trackball or a combination thereof and to a display 7 such as a monitor. The computer 2 can acquire data, such as an image dataset, via the interface 4. The memory 5 can store the acquired data and store data calculated by the central processing unit 3.

FIG. 2 shows a flow diagram of a data processing method for calculating a medical display image. In step S01, the CPU 3 acquires at least one image dataset representing a medical image of a patient, for example via the interface 4 or from the memory 5. In the following step S02, the CPU 3 acquires a patient-specific information dataset representing patient-specific information, for example via the interface 4, from the memory 5 or from the input device 6.

In step S03, the CPU 3 acquires a plurality of templates, for example via the interface 4 or from the memory 5. Each template defines rules and/or settings for calculating a display image from an image dataset. In step S04, the CPU 3 acquires a lookup table comprising a plurality of lookup table patient-specific information datasets, wherein the lookup table comprises links between the plurality of lookup table patient-specific information datasets and the plurality of templates such that each lookup table patient-specific information dataset has an associated template.

In the following step S05, the CPU 3 determines a lookup table patient-specific information dataset corresponding to the acquired patient-specific information dataset acquired in step S02. In particular, it is determined whether or not one of the lookup table patient-specific information datasets equals the acquired patient-specific information datasets. If this is not the case, the lookup table patient-specific information dataset being most similar to the acquired patient-specific information dataset is determined.

In step S06, the CPU 3 determines the template which is associated with the lookup table patient-specific information dataset acquired in step S05. In step S07, a display image is calculated from the image dataset acquired in step S01 and on the basis of the template determined in step S06.

In the present example, the patient has a tumor which is classified in accordance with ICD tumor codes. The patient-specific information dataset comprises the code associated with the tumor of the patient.

In step S01, two image datasets are acquired, one CT image dataset and one MR image dataset. The template determined in step S06 comprises information on a sectional plane of the image datasets which is to be visualized in the display image. The template further comprises information about a zoom factor, windowing parameters and how two views, one generated from the CT image dataset and one generated from the MR image dataset, have to be arranged in the display image.

In step S07, the CPU 3 calculates a two-dimensional view of the tumor from the CT image dataset on the basis of the sectional plane defined in the template. The view is centered about the tumor and the center of the tumor lies in the sectional plane. The data from the CT image dataset is transformed into a grey scale distribution in the view in accordance with the windowing parameters defined in the template. The size of the area around the tumor which is shown in the view depends on the zoom factor defined in the template and the size of the view in the display image, which is also defined in the template. The view is then placed in the display image at a position as defined in the template. In analogy, a second view is generated from the MR image dataset on the basis of the information comprised in the template. The display image calculated in step S07 thus shows two views of the tumor generated from different image datasets.

As an option, the tumor is highlighted in the views within the display image, for example by using a predetermined color. As another option, further information is included in the display image, such as the trajectory of a biopsy needle which can be used for treating the tumor or the path of a treatment beam.

In step S08, the display image is output on the monitor 7. As an alternative, the display image can be stored in the memory 5, provided to another device via the interface 4 or provided to a portable electronic display device which can store and/or display the display image.

The invention claimed is:

1. A data processing method for calculating a medical display image to be displayed on a display device that has a first dynamic range, comprising:
   acquiring at least one image dataset representing a medical image of an associated patient, the at least one image dataset having a second dynamic range, the second dynamic range of the at least one image dataset being greater than the first dynamic range of the display device, and the at least one image dataset depicting an object of a particular type within the associated patient;
   acquiring a patient-specific information dataset representing patient-specific information;
   automatically selecting a template from a plurality of templates in accordance with the acquired patient-specific information, the template being a dataset comprising settings and/or rules for calculating the display image from the at least one image dataset, the template comprising settings and/or rules for windowing parameters, the windowing parameters being a window representing a range of interest of the second dynamic range of the at least one image dataset, and the range of interest being a sub-range of the second dynamic range of the at least one image dataset depending on the particular type of the object depicted by the medical image; and
   calculating the display image to be displayed on the display device in the first dynamic range of the display device from the at least one image dataset on the basis of the template, the calculating the display image comprising an uncompressed mapping of the sub-range of the second dynamic range of the at least one image dataset to the first dynamic range of the display device based on the windowing parameters,
   wherein the patient-specific information comprises information on at least one of a medical indication, a prior treatment, a prior disease, a planned treatment, a following treatment step, and an applied contrast agent.

2. The method according to claim 1, wherein the medical indication is represented by a type or a category of a disease of the associated patient, wherein the disease is a tumor.

3. The method according to claim 2, wherein calculating the display image further comprises highlighting the contour of the tumor in the display image.

4. The method according to claim 1, wherein when the image dataset represents a three-dimensional medical image, the calculating the display image further comprises selecting a sectional plane in accordance with the template.

5. The method according to claim 1, wherein when a plurality of image datasets have been acquired, the calculating the display image further comprises selecting at least one of the image datasets in accordance with the template for the calculating the display image.

6. The method according to claim 1, wherein the calculating the display image further comprises selecting at least one of a zoom factor and a cut-out in accordance with the template.

7. The method according to claim 1, further comprising acquiring a lookup table comprising a plurality of lookup table patient-specific information datasets and of assigning one of the plurality of the templates to each of the lookup table patient-specific information datasets, wherein the template used for the calculating the display image is selected using the lookup table.

8. The method according to claim 7, wherein selecting the template comprises calculating distance measures between the acquired patient-specific information dataset and each of the lookup table patient-specific information datasets, determining the lookup table patient-specific information dataset with the lowest distance measure and selecting the template associated with this lookup table patient-specific information dataset.

9. The method according to claim 1, wherein the diagnosis-specific information comprises information on at least one of a landmark, a functional area, the associated patient's anatomy, a therapy, a trajectory, and an access plan.

10. The method according to claim 1, further comprising providing the display image to a portable electronic display device.

11. The method according to claim 10, further comprising linking the display image to a calendar entry in the portable electronic display device and displaying the display image on the portable electronic display device when the calendar entry is opened.

12. The method according to claim 1, further comprising acquiring two image datasets, wherein one image dataset is a computed tomography image dataset and one image dataset is a magnetic resonance image dataset.

13. The method according to claim 1, wherein the template further comprises rules and/or settings for highlighting a contour of a tumor from the at least one image dataset.

14. The method according to claim 1, wherein the template further comprises rules and/or settings for selecting a sectional plane from the at least one image dataset.

15. The method according to claim 1, wherein the template further comprises rules and/or settings for selecting at least one of a zoom factor or a cut-out from the at least one image dataset.

16. The method according to claim 1, wherein the template further comprises rules and/or settings for adding diagnosis-specific information to the display image.

17. The method according to claim 1, wherein:
   the windowing parameters comprises a plurality of windows of the second dynamic range of the at least one image dataset, and the calculating the display image comprises individually adapting each of the plurality of windows of the second dynamic range of the at least one image dataset to the first dynamic range of the display device.

18. The method according to claim 1, wherein the particular type of the object is a bone, an organ, or a tumor.

19. A non-transitory computer readable storage device storing a program for calculating a medical display image to be displayed on a display device that has a first dynamic range, which, when executed by an associated computer or loaded by an associated computer, causes the associated computer to:
   acquire at least one image dataset representing a medical image of an associated patient, the at least one image dataset having a second dynamic range, the second dynamic range of the at least one image dataset being greater than the first dynamic range of the display device, and the at least one image dataset depicting an object of a particular type within the associated patient;
   acquire a patient-specific information dataset representing patient-specific information;
   automatically select a template from a plurality of templates in accordance with the acquired patient-specific information, the template being a dataset comprising settings and/or rules for calculating a display image from the at least one image dataset, the template comprising settings and/or rules for windowing parameters, the windowing parameters being a window representing a range of interest of the second dynamic range of the at least one image dataset, and the range of interest being a sub-range of the second dynamic range of the at least one image dataset depending on the particular type of the object depicted by the medical image; and calculate the display image to be displayed on the display device in the first dynamic range of the display device from the at least one image dataset on the basis of the template, the calculating the display image comprising an uncompressed mapping of the sub-range of the second dynamic range of the at least one image dataset to the first dynamic range of the display device based on the windowing parameters, wherein the patient-specific information comprises information on at least one of a medical indication, a prior treatment, a prior disease, a planned treatment, a following treatment step, and an applied contrast agent.

20. A device for calculating a medical display image to be displayed on a display device having a first dynamic range, the device comprising a processor for causing the device to:

acquire at least one image dataset representing a medical image of a patient, the at least one image dataset having a second dynamic range, the second dynamic range of the at least one image dataset being greater than the first dynamic range of the display device, and the at least one image dataset depicting an object of a particular type within the associated patient;

acquire a patient-specific information dataset representing patient-specific information;

automatically select a template from a plurality of templates in accordance with the acquired patient-specific information, the template being a dataset comprising settings and/or rules for calculating a display image from the at least one image dataset, the template comprising settings and/or rules for windowing parameters, the windowing parameters being a window representing a range of interest of the second dynamic range of the at least one image dataset, and the range of interest being a sub-range of the second dynamic range of the at least one image dataset depending on the particular type of the object depicted by the medical image; and calculate the display image to be displayed on the display device in the first dynamic range of the display device from the at least one image dataset on the basis of the template, the calculating the display image comprising an uncompressed mapping of the sub-range of the second dynamic range of the at least one image dataset to the first dynamic range of the display device based on the windowing parameters, wherein the patient-specific information comprises information on at least one of a medical indication, a prior treatment, a prior disease, a planned treatment, a following treatment step, and an applied contrast agent.

* * * * *